(12) United States Patent
Gavriely et al.

(10) Patent No.: US 8,366,739 B2
(45) Date of Patent: Feb. 5, 2013

(54) MOTION CONTROL DEVICES

(75) Inventors: Noam Gavriely, Haifa (IL); Oren Gavriely, Haifa (IL); Benny Rousso, Rishon-LeZion (IL)

(73) Assignee: OHK Medical Devices Ltd., Haifa (IL)

( * ) Notice: Subject to any disclaimer, the term of this patent is extended or adjusted under 35 U.S.C. 154(b) by 687 days.

(21) Appl. No.: 12/361,567

(22) Filed: Jan. 29, 2009

(65) Prior Publication Data

US 2009/0254012 A1  Oct. 8, 2009

Related U.S. Application Data

(60) Provisional application No. 61/006,758, filed on Jan. 30, 2008.

(51) Int. Cl.
*A61B 17/00* (2006.01)
(52) U.S. Cl. ............................................. 606/203
(58) Field of Classification Search .......... 606/201–204; 223/111–112
See application file for complete search history.

(56) References Cited

U.S. PATENT DOCUMENTS

| | | | |
|---|---|---|---|
| 34,112 A | 1/1862 | Lambert | |
| 35,038 A | 4/1862 | Pierce | |
| 800,467 A * | 9/1905 | Myers | 602/5 |
| 814,795 A * | 3/1906 | Myers | 602/6 |
| 1,279,784 A | 3/1914 | Stoplek | |
| 1,992,344 A * | 2/1935 | Alhadate | 602/63 |
| 2,149,149 A * | 2/1939 | Scheinberg | 450/111 |
| 2,320,179 A * | 5/1943 | Gray | 600/499 |
| 2,333,237 A * | 11/1943 | Erekson | 606/203 |
| 2,443,115 A * | 6/1948 | Park | 223/111 |
| 2,574,873 A * | 11/1951 | Jobst | 602/63 |
| 2,582,648 A * | 1/1952 | Mowbray | 36/8.1 |
| 2,604,098 A | 7/1952 | Kranc | |
| 2,796,207 A * | 6/1957 | Young | 223/111 |
| 2,908,057 A * | 10/1959 | Blanco | 24/3.13 |
| 3,070,271 A * | 12/1962 | Kennedy, Sr. | 223/111 |
| 3,079,917 A * | 3/1963 | Pate | 128/206.27 |
| 3,095,873 A | 7/1963 | Edmunds | |
| 3,097,644 A * | 7/1963 | Parker | 602/79 |
| 3,227,335 A * | 1/1966 | Minnema et al. | 223/111 |
| 3,279,459 A * | 10/1966 | Schenker | 600/499 |
| 3,401,856 A * | 9/1968 | Berlin | 223/111 |
| 3,452,907 A * | 7/1969 | MacLauchlan | 223/111 |

(Continued)

FOREIGN PATENT DOCUMENTS

| BG | 99835 U | 3/1997 |
|---|---|---|
| CN | 1602170 | 3/2005 |

(Continued)

OTHER PUBLICATIONS

PCT Search Report for PCT/IL2002/00992 transmitted.

(Continued)

*Primary Examiner* — Darwin Erezo
(74) *Attorney, Agent, or Firm* — Graeser Associates International Inc; Dvorah Graeser

(57) ABSTRACT

Disclosed is a device for exsanguinating a portion of an extremity. The device comprises an elastic torus configured to ensanguine a limb when surrounding an extremity and pulled at a first linear rate in a first direction; and at least one elongate attachment element mechanically coupled to the torus to convey pulling force from the handle to the torus, wherein the a length of the elongate attachment element between the handle and the torus elongates at a different rate than the first rate, during the pulling.

12 Claims, 12 Drawing Sheets

U.S. PATENT DOCUMENTS

| | | | |
|---|---|---|---|
| 3,454,010 A * | 7/1969 | Miller et al. | 606/202 |
| 3,935,984 A | 2/1976 | Lichowsky | |
| 3,968,792 A * | 7/1976 | Small | 128/856 |
| 4,206,765 A | 6/1980 | Huber | |
| 4,243,039 A | 1/1981 | Aginsky | |
| 4,441,504 A | 4/1984 | Peterson | |
| 4,479,494 A | 10/1984 | McEwen | |
| 4,495,941 A * | 1/1985 | Rathvon et al. | 602/1 |
| 4,520,820 A | 6/1985 | Kitchin | |
| 4,548,198 A | 10/1985 | Manes | |
| 4,566,436 A * | 1/1986 | Loefqvist | 128/898 |
| 4,577,622 A * | 3/1986 | Jennings | 601/134 |
| 4,637,394 A * | 1/1987 | Racz et al. | 606/202 |
| 4,738,249 A * | 4/1988 | Linman et al. | 601/152 |
| 4,765,520 A * | 8/1988 | Barton | 223/111 |
| 4,770,175 A | 9/1988 | McEwen | |
| 4,828,310 A * | 5/1989 | Schmidt et al. | 294/153 |
| 4,848,324 A * | 7/1989 | Gavriely | 601/134 |
| 4,869,265 A | 9/1989 | McEwen | |
| 4,872,463 A * | 10/1989 | Nishizono | 128/844 |
| 4,972,850 A * | 11/1990 | Broad, Jr. | 128/844 |
| 4,980,150 A | 12/1990 | Keith | |
| 5,048,536 A | 9/1991 | McEwen | |
| 5,163,448 A * | 11/1992 | Foldesy | 128/844 |
| 5,181,522 A | 1/1993 | McEwen | |
| 5,193,549 A | 3/1993 | Bellin | |
| 5,203,786 A | 4/1993 | Vernick | |
| 5,226,874 A | 7/1993 | Heinz | |
| 5,304,202 A * | 4/1994 | Stahl | 606/203 |
| 5,312,431 A | 5/1994 | McEwen | |
| 5,327,911 A * | 7/1994 | Pien | 128/844 |
| 5,351,694 A | 10/1994 | Davis | |
| 5,351,698 A * | 10/1994 | Wheeler et al. | 128/844 |
| 5,376,067 A * | 12/1994 | Daneshvar | 602/58 |
| 5,383,893 A * | 1/1995 | Daneshvar | 606/201 |
| 5,411,518 A * | 5/1995 | Goldstein et al. | 606/202 |
| 5,413,582 A | 5/1995 | Eaton | |
| 5,454,831 A | 10/1995 | McEwen | |
| 5,556,073 A | 9/1996 | Wawro | |
| 5,578,055 A | 11/1996 | McEwen | |
| 5,582,689 A | 12/1996 | Van Haag | |
| 5,606,982 A * | 3/1997 | Piotti | 128/842 |
| 5,607,448 A * | 3/1997 | Stahl et al. | 606/203 |
| 5,620,001 A * | 4/1997 | Byrd et al. | 606/202 |
| 5,626,269 A * | 5/1997 | Duarte | 223/112 |
| 5,649,954 A | 7/1997 | McEwen | |
| 5,669,390 A * | 9/1997 | McCormick et al. | 600/499 |
| 5,695,513 A | 12/1997 | Johnson | |
| 5,695,520 A * | 12/1997 | Bruckner et al. | 606/204 |
| 5,741,295 A | 4/1998 | McEwen | |
| 5,876,436 A * | 3/1999 | Vanney et al. | 623/2.39 |
| 5,893,871 A * | 4/1999 | Tanaka | 606/204 |
| 5,894,970 A * | 4/1999 | Belkin et al. | 223/112 |
| 6,149,666 A | 11/2000 | Marsden | |
| 6,361,496 B1 * | 3/2002 | Zikorus et al. | 600/437 |
| 6,523,729 B1 * | 2/2003 | Gardon-Mollard | 223/112 |
| 6,682,547 B2 | 1/2004 | McEwen | |
| 6,732,736 B2 * | 5/2004 | Sanchez | 128/844 |
| 6,746,470 B2 | 6/2004 | McEwen | |
| 7,077,814 B2 | 7/2006 | Mollenauer | |
| 7,527,057 B2 * | 5/2009 | Fecteau et al. | 128/206.27 |
| 7,604,651 B1 | 10/2009 | Harris | |
| 7,648,404 B1 * | 1/2010 | Martin | 441/70 |
| 7,699,195 B2 * | 4/2010 | Scott | 223/111 |
| 7,854,748 B2 * | 12/2010 | Gavriely | 606/203 |
| 7,854,941 B2 | 12/2010 | Urban | |
| 2003/0065357 A1 | 4/2003 | Dedo | |
| 2003/0139766 A1 | 7/2003 | McEwen | |
| 2004/0111047 A1 | 6/2004 | Reid | |
| 2005/0080450 A1 * | 4/2005 | Gavriely | 606/201 |
| 2005/0087115 A1 * | 4/2005 | Martin | 114/39.19 |
| 2005/0087573 A1 * | 4/2005 | Unsworth et al. | 223/112 |
| 2005/0113866 A1 | 5/2005 | Heinz | |
| 2005/0267518 A1 | 12/2005 | Wright | |
| 2006/0025807 A1 | 2/2006 | Licata | |
| 2007/0191881 A1 | 8/2007 | Amisar | |
| 2008/0081020 A1 | 4/2008 | Huang | |
| 2009/0254012 A1 * | 10/2009 | Gavriely et al. | 601/134 |

FOREIGN PATENT DOCUMENTS

| | | |
|---|---|---|
| EP | 1453434 | 9/2004 |
| EP | 1453424 | 6/2006 |
| GB | 713132 | 8/1954 |
| GB | 206271 | 7/2011 |
| JP | 59-183216U.M. | 10/1984 |
| JP | 50-183216 | 12/1984 |
| JP | 2001161742 | 6/2001 |
| WO | WO2005079691 | 9/2005 |
| WO | WO2006071251 | 7/2006 |

OTHER PUBLICATIONS

Office Action dated Sep. 19, 2007 for AU application 2002360196.
Crenshaw et al, Wide tourniquets cuff more effective at lower inflation pressures, Acta Orthopaedica, Aug. 1, 1988, pp. 447-451, vol. 59 No. 4.
Office Action dated Mar. 17, 2010 for CA application 2469283.
Office Action dated Dec. 26, 2008 for JP application 2003-550674.
PCT Search Report for PCT/IL2002/00992.
Office Action dated Jan. 15, 2009 for IN application 1287/CHENP/2004.
Office Action dated Sep. 16, 2005 for CN application 02824809.0.

* cited by examiner

MOTION CONTROL DEVICES

RELATED APPLICATIONS

The present application claims the benefit of U.S. Provisional Patent Application No. 61/006,758, filed on Jan. 30, 2008, the disclosure of which is incorporated herein by reference.

FIELD AND BACKGROUND OF THE INVENTION

The present invention, in some embodiments thereof, relates to devices configured to control the motion of a torus along an extremity and, more particularly, but not exclusively, to handles and straps that control torus motion.

A bloodless extremity during a surgical procedure is highly desirable in helping the surgeon identify tissue layers, anatomic landmarks and biological structures.

To attempt to exsanguinate the extremity and render a bloodless surgical site, a first sterile assistant typically elevates the extremity above the heart while a second sterile assistant wraps an elastic bandage in a spiral fashion from the distal portion of the extremity to proximal to the surgical site.

The elastic wrap drives some of the blood in the extremity proximal to the surgical site and, to prevent a flow of blood during surgery, a pneumatic tourniquet proximal to the surgical site is inflated to a pressure of between 150 and 500 millimeters of mercury (mm Hg). The elastic bandage is then removed and the surgeon makes a first incision into the surgical site.

The first incision, however, is often accompanied by a release of residual blood remaining in the extremity distal to the tourniquet. The residual blood often covers and obstructs visualization of the surgical site. Lavage and copious sponging by a sterile assistant renders a relatively bloodless, but wet, surgical site.

U.S. patent application Ser. No. 10/498,369, now published as U.S. Patent Application Publication No. 200510080450A1 (Gavriely) teaches a tubular sock and elastic annulus that roll along the extremity to exsanguinate the extremity.

SUMMARY OF THE INVENTION

According to one aspect of some embodiments of the invention, there is provided a device for exsanguinating a portion of an extremity. The device comprises an elastic torus configured to ensanguine a limb when surrounding an extremity and pulled at a first linear rate in a first direction; and at least one elongate attachment element mechanically coupled to the torus to convey pulling force from the handle to the torus, wherein the a length of the elongate attachment element between the handle and the torus elongates at a different rate than the first rate, during the pulling.

According to some embodiments of the invention, the elastic torus is configured to twistingly rotate while moving linearly.

According to some embodiments of the invention, the at least one application strap comprises at least one elongate handle having a curved end.

According to some embodiments of the invention, the at least one elongate handle is configured to move the elastic torus in a second linear direction.

According to some embodiments of the invention, the at least one application strap is connected to at least one rotatable take-up reel.

According to some embodiments of the invention, the device includes an elongate flexible tube wound around the elastic torus, the elongate flexible tube configured to progressively unwind from the elastic torus and surround the extremity portion as the elastic torus is moved in the first linear direction.

According to some embodiments of the invention, the device includes an elongate flexible tube wound around the elastic torus and the at least one application strap comprises at least two application straps: at least one external application strap configured to be juxtaposed along an external longitudinal surface of the elongate tube, and at least one internal application strap configured to be juxtaposed along an internal longitudinal surface of the elongate tube.

According to some embodiments of the invention, the elongate flexible tube is configured to progressively unwind from the elastic torus and surround the extremity portion as the elastic torus is moved in the first linear direction.

According to some embodiments of the invention, the at least two application straps are configured to move the elastic torus in a second linear direction.

According to some embodiments of the invention, moving the elastic torus in the second linear direction causes the elongate flexible tube to rewind around the elastic torus.

According to some embodiments of the invention, the at least one external application strap and the at least one internal application strap comprise at least one continuum.

According to some embodiments of the invention, the at least one continuum is slidingly connected to a handle.

According to some embodiments of the invention, the at least one continuum is connected to at least one rotatable take-up reel.

According to some embodiments of the invention, the at least one rotatable take-up reel takes up the continuum while rotating in a first direction and in a second direction.

According to another aspect of some embodiments of the invention, there is provided a device for exsanguinating a portion of an extremity, the device including: an elastic torus configured to surround an elongate element and move linearly while applying an exsanguinating pressure to the extremity, and at least one handle operatively associated with the elastic torus, the at least one handle configured to move the elastic torus along the extremity in a proximal direction and in a distal direction.

According to some embodiments of the invention, the at least one handle is configured to optimally roll the torus in a proximal direction when an angle between the extremity and the at least one handle is between 0 and 60 degrees.

According to some embodiments of the invention, the at least one handle is configured to optimally roll the torus in a distal direction when an angle between the extremity and the at least one handle handles is between 120 and 180.

According to some embodiments of the invention, the elastic torus is configured to twistingly rotate while moving linearly.

According to some embodiments of the invention, the at least one handle comprises at least one elongate rigid element having a curved portion configured to twistingly rotate the elastic torus.

According to some embodiments of the invention, the device includes an elongate flexible tube wound around the elastic torus, the elongate flexible tube configured to progressively unwind from the elastic torus and surround the extremity portion as the elastic torus is moved in a proximal direction.

According to some embodiments of the invention, the elongate flexible tube is configured to progressively rewind on the elastic torus as the elastic torus is moved in a distal direction.

According to some embodiments of the invention, the at least one handle includes at least one external strap configured to be juxtaposed along an external longitudinal surface of the elongate tube, and at least one internal strap configured to be juxtaposed along an internal longitudinal surface of the elongate tube.

According to some embodiments of the invention, the at least one handle includes one take-up reel configured to take-up at least a portion of the one external strap.

According to some embodiments of the invention, the one take-up reel is additionally configured to release at least a portion of the one internal strap.

According to some embodiments of the invention, the one internal strap forms a continuum with the one external strap and the at least one handle is slidingly juxtaposed along the continuum.

According to a further aspect of some embodiments of the invention, there is provided a method for forming a torus that encircles an extremity portion, the method including: juxtaposing an external strap along an external longitudinal surface of an elongate tube, rolling the elongate tube into a torus, placing the torus around an annular cross-sectional portion of an extremity portion, pulling the one external strap, unrolling the torus into an elongate tube surrounding the extremity while exsanguinating a portion of the extremity, juxtaposing an internal strap along an internal longitudinal surface of an elongate tube portion, pulling the one internal strap, and rerolling the elongate tube into a torus.

According to some embodiments of the invention, the method includes forming a continuum between the one external strap and the one internal strap, pulling the continuum in a first direction to unroll the elongate tube from the torus, and pulling the continuum in a second direction to reroll the elongate tube into a torus.

According to still another aspect of some embodiments of the invention, there is provided a method for exsanguinating an extremity portion, the method including juxtaposing an external strap along an external longitudinal surface of an elongate tube, rolling the elongate tube into a torus, placing said torus around an annular cross-sectional portion of an extremity portion, pulling said strap and exsanguinating a portion of said extremity while unrolling said torus into an elongate tube around said extremity at a first rate, and lengthening said external strap at a different rate than said first rate.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

As used herein, the terms "comprising" and "including" or grammatical variants thereof are to be taken as specifying the stated features, integers, steps or components but do not preclude the addition of one or more additional features, integers, steps, components or groups thereof. This term encompasses the terms "consisting of" and "consisting essentially of".

The phrase "consisting essentially of" or grammatical variants thereof when used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed composition, device or method.

The term "method" refers to manners, means, techniques and procedures for accomplishing a given task including, but not limited to, those manners, means, techniques and procedures either known to, or readily developed from known manners, means, techniques and procedures by practitioners of orthopedic biomechanics.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 5A-B and 10 show a torus having hooked application handles, according to embodiments of the invention.

DESCRIPTION OF EMBODIMENTS OF THE INVENTION

Figure 1:
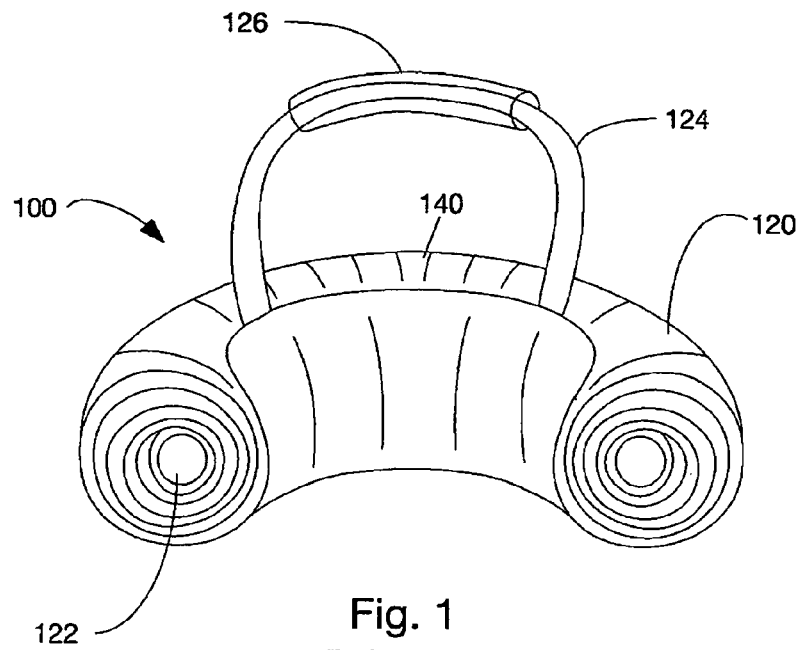
FIGS. 1-3 show a known torus exsanguinating an extremity portion.

The present invention, in some embodiments thereof relates to devices configured to control the motion of a torus along an extremity and, more particularly, but not exclusively, to handles that control torus motion.

The motion of an exsanguinating torus is controlled by a sterile operator in a surgical theater by using application straps that extend in a proximal direction and pull the torus up the extremity. As the torus proceeds up the extremity, a sterile elastic tube unrolls while encircling the extremity and the application straps lengthen according to the distance the torus has traveled, possibly presenting a hazard for contaminating the surgical field.

The present invention contemplates a variety of application strap embodiments that serve to shorten and/or fix the length of the application straps.

In some embodiments, pulling handles include uptake reels to take up much of the extending application straps. Some embodiments include one uptake reel for each application strap so that four application straps require four uptake reels. In other embodiments, one uptake reel takes up all application straps.

In addition to the above embodiments, there are application strap embodiments contemplated that guide movement of the exsanguinating torus both in a proximal direction and in a distal direction. One embodiment, for example, includes uptake reels whose rotation are reversible so that the application strap can be used to pull the torus both in a proximal direction and in a distal direction; in both cases, the uptake reel prevents undesirable lengthening of the application straps.

In other embodiments, an application strap is provided that extends to both sides of the elastic tube so that as the mobile torus unwinds and the application strap lengthens along on the outer surface of the elastic tube, the same length of strap is deposited along the extremity on the inner surface of the elastic tube. In this manner, the application straps maintain a constant length during application. Further, by reversing the pull of the application straps, the torus is pulled in a distal direction along the limb with the outer surface application strap rolling into the torus as the inner application strap lengthens.

In still further embodiments, the torus assembly is mobilized using relatively rigid handles that are separate from the torus. The rigid handles include curved members that contact the torus and pull the torus in either proximal or distal direction.

The principles and operation of devices configured to control the motion of a torus along an extremity according to the present invention, may be better understood with reference to the drawings and accompanying descriptions.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Referring now to the drawings:

Shown in FIG. 1 is an extremity exsanguination assembly 100, shown in cross section, similar to a torus device shown in the above-noted U.S. Patent Application No. 20050080450A1.

Torus assembly 100 includes an elastic tube 120 folded around a flexible elastic ring 122, herein torus 122, along with application straps 124. According to some embodiments of the invention, torus 122 comprises a single homogenous solid ring of an elastic material, for example rubber.

Figure 2:
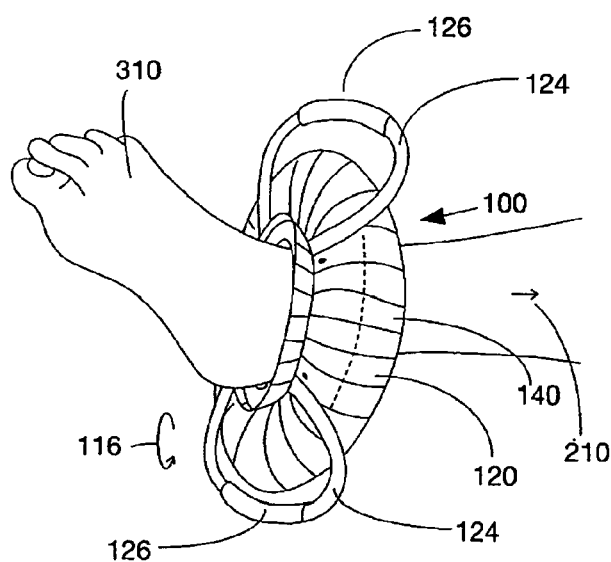
Figure 3:
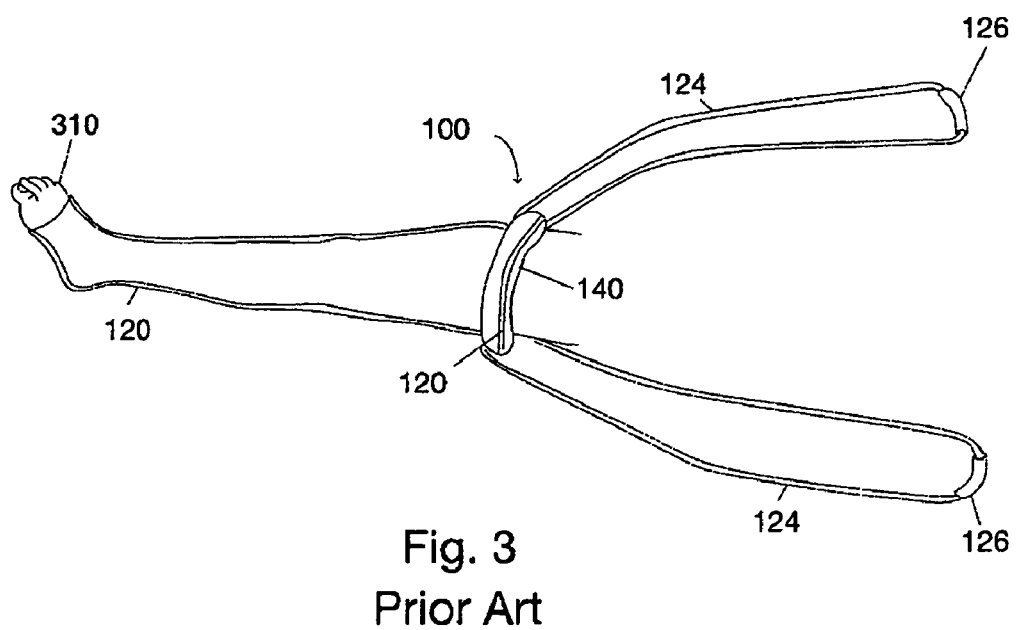

As seen in FIG. 2, application straps 124 and an associated handle 126 are used to roll torus assembly 100 in a rotational direction 116 along an extremity 310 while elastic tube 120 unrolls from around torus 122 to encircle extremity 310. The rolling motion of torus 122 in rotational direction 116, or the opposite thereof, is referred to herein as twisting rotation.

As seen in FIG. 31 as torus assembly 100 rolls in a proximal direction, torus 122 (not shown) and the wound remainder of elastic tube 120 exert pressure on extremity 310 that is higher than the arterial, capillary and venous blood pressure.

The pressure from torus 122 and the wound remainder of elastic tube 120 squeezes extremity 310 in progression from a distal position to a more proximal position, causing blood to move proximal to torus 122, leaving the distal portion of extremity 310 substantially bloodless.

The constrictive pressure generated by torus 122 and elastic tube 120 is higher than the arterial blood pressure yet lower than the pressure that may cause crush injury to the tissues beneath it.

After torus assembly 100 is located proximal to the surgical site, torus 122 is left in place to prevent blood from entering extremity 310 as would the above-noted tourniquet.

During movement of torus assembly 100, application straps 124 continually extend and lengthen in a proximal direction so that as torus 122 reaches the thigh area of extremity 310, application straps 124 may extend into a non-sterile area. A sterile assistant must therefore continually bunch up application straps 124 to prevent intrusion into the non-sterile area; thereby risking personal contamination and possibly bringing contaminants into the sterile field.

Figure 4:
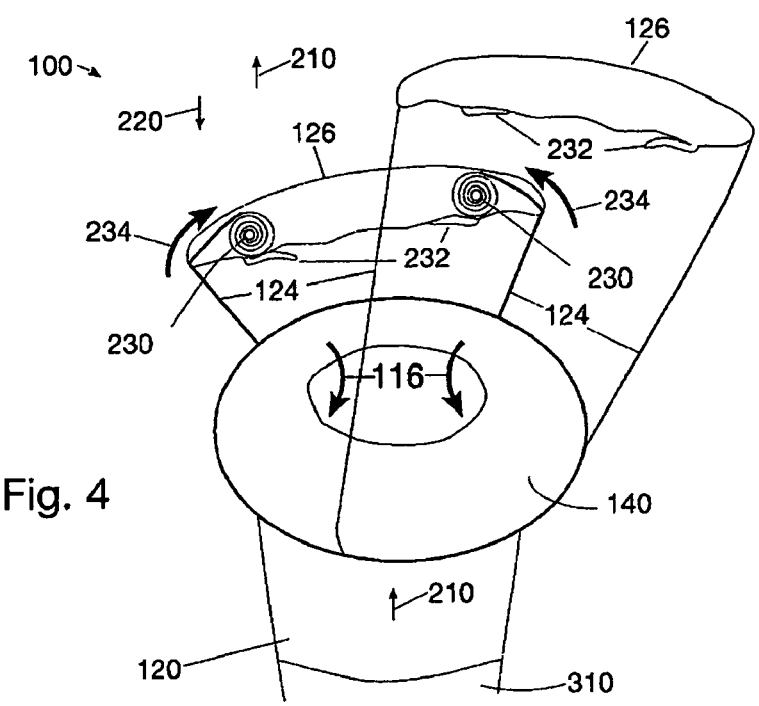
FIGS. 4, 5, and 6A-B show torus configurations with application straps connected to uptake reels, according to embodiments of the invention.

As noted above, several embodiments of torus assembly 100 are presented which include application straps 124 that do not fully extend during proximal movement. Just one possible example of straps that do not fully extend is shown in FIG. 4 in which application straps 124 of torus assembly 100 connected to spring loaded uptake reels 230.

Dual Uptake Reels

During operation of torus assembly 100, as handle 126 is pulled in a proximal direction 210, release levers 232 press against portions of applications straps 124 that are wound around spring loaded uptake reels 232, thereby preventing rotation of spring loaded uptake reels 232.

With each pull in proximal direction 210, application straps 124 cause an elastic tube roll 140 to twistingly rotate in direction 116. After application straps 124 have extended a moderate distance above elastic tube roll 140, for example near a non-sterile area, the operator presses release levers 232 to release spring loaded uptake reels 230 and moves handles 126 in a distal direction 220.

As handles 126 are moved in distal direction 220, spring-loaded uptake reels 230 rotate in a clockwise direction 234 to take up slack along application straps 124, thereby winding application straps 124 onto spring loaded uptake reels 230.

To continue applying elastic tube 120 in proximal direction 210, the operator releases release levers 232 to again press against the wound portion of application straps 124 and resumes pulling handles 126 in a proximal direction in direction 210.

Some operators may find a possible drawback in that controlling dual levers 232 on each handle 126 could be cumbersome. In some embodiments, a single lever 232 embodiment is presented which provides control with single lever 232.

Single Uptake Reel

Figure 5:
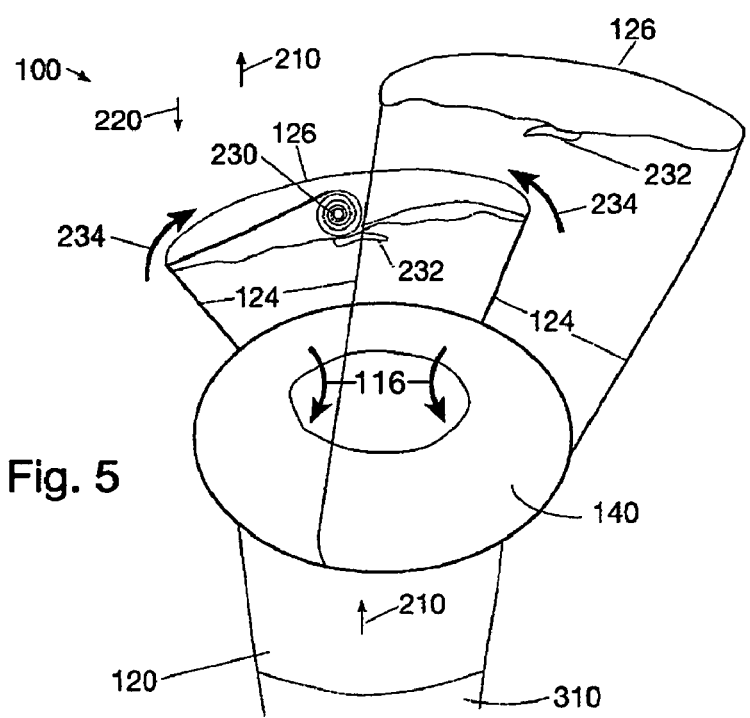

FIG. 5 shows single uptake reel 230 to which two application straps 124 are attached. As handle 126 is pulled in a proximal direction 210, release lever 232 presses against application straps 124 that are wound around spring loaded uptake reels 230 and elastic tube roll 140 unwinds in the above-noted manner.

Upon pressing release lever 232 and moving handles 126 in distal direction 220, noted-above, spring-loaded uptake reel 230 rotates clockwise 234 to take up slack along two application straps 124.

It has been possibly potentially determined that embodiments of torus assembly 100 having spring loaded reels 230 and levers 232, may prevent extension of application straps 124 into a non-sterile area.

Still further embodiments are contemplated that may be advantageous in specific surgical procedures, such as during arterial anastomosis.

During the surgery, the surgeon may wish to confirm the integrity of an anastomosed artery by temporarily allowing blood pressure to increase in the anastomosed artery. Following confirmation, the surgeon may wish to again exsanguinate the surgical area in order to continue with further surgical procedures.

Rolling torus assembly 100 in distal direction 220 to temporarily allow an increase in blood pressure may require two sterile operators; a first sterile operator to roll torus assembly 100 in a distal direction while a second sterile operator holds handles 126 and presses release lever 232, thereby allowing application straps 124 to be rolled into elastic tube roll 140.

In such applications it may be desirable to provide configurations of torus assembly 100 in which handles 126 allow unrolling and rolling of torus assembly 100 by a single operator.

Reversible Uptake Reels

Figure 6A:
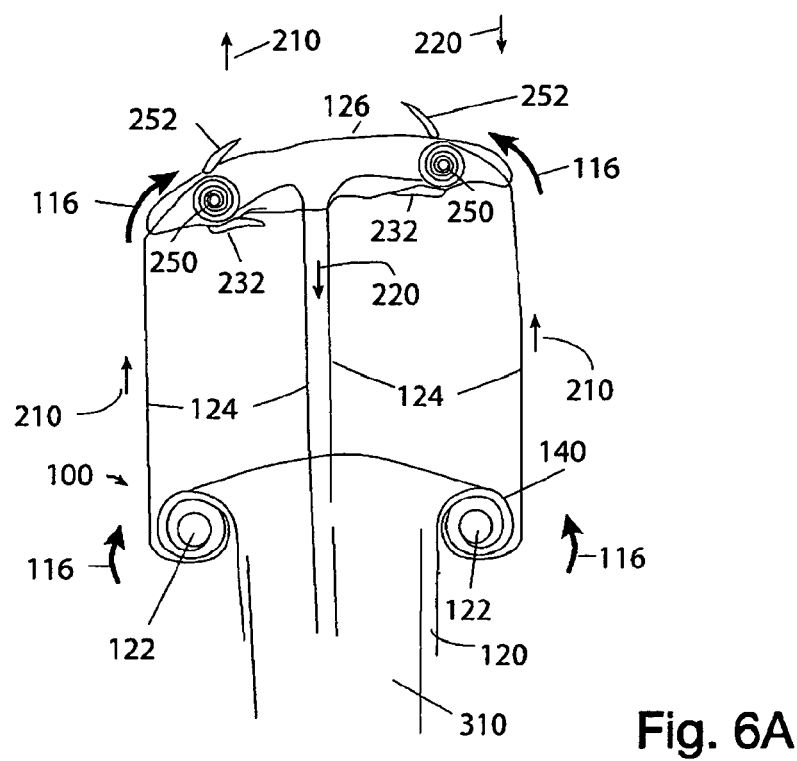

Just one embodiment of a handle that guides a torus both in a proximal direction and in a distal direction is shown in FIG. 6A in which torus assembly 100 includes reversible uptake reels 250, which are spring-loaded in two directions. Initially, the operator activates release levers 232 so that release levers 232 automatically press against application straps 124 that are wound around reversible uptake reel 250, preventing movement of application straps 124.

In pulling torus assembly 100 in a proximal direction, handle 126 is pulled in proximal direction 210 with periodic pressing of lever 232 and distal movement 220 of handles, as noted above, to take up application straps 124 around reversible uptake reel 250.

Figure 6B:
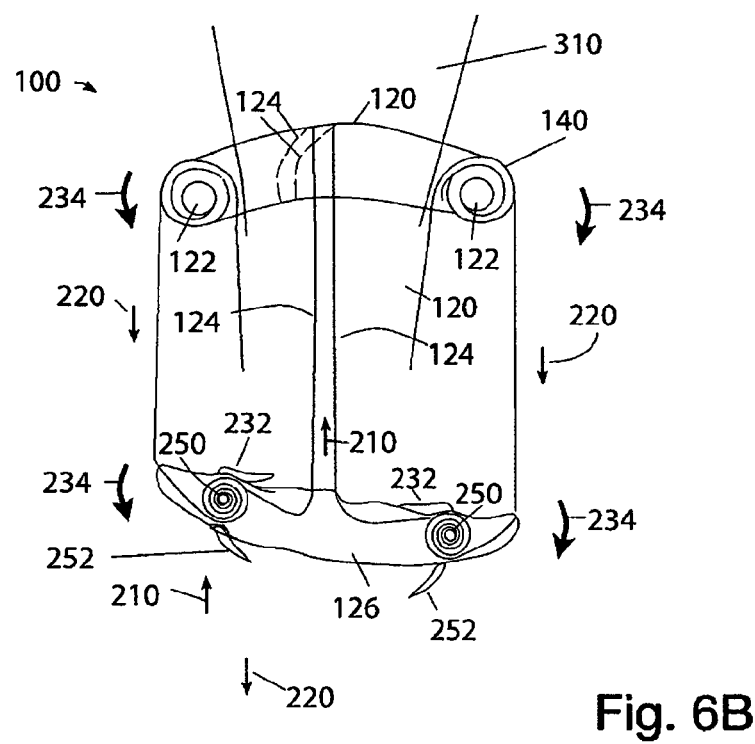

As seen in FIG. 6B, to reroll elastic tube 120 into elastic tube roll 140, the operator activates reuptake levers 252 to press against application straps 124 that are wound around reversible uptake reels 250, thereby preventing movement of application straps 124 and reversible uptake reels 250.

As handle 126 is pulled in distal direction 220, application straps 124 are pulled in a distal direction 220, causing elastic tube roll 140 to rotate clockwise 234, thereby rolling elastic tube roll 140 in a distal direction 220 while elongating application straps 124.

To retract elongated section of application straps 124, the operator presses reuptake levers 252 so that reversible uptake reels 250 become free so that tension-loaded reels 250 rotate in clockwise direction 234 to take up slack along application straps 124.

If necessary to re-exsanguinate the proximal portion of extremity 310, handle 126 is positioned proximally 2101 release levers 232 are activated and the above-noted steps related to pulling handle in proximal direction 210 are repeated.

There are still further embodiments of torus assembly 100 in which rotation twisting movement both in a proximal direction and in a distal direction is controlled by alternative mechanism.

Strap Continuum Torus

Just one such alternative mechanism is shown in FIGS. 7A-8B which includes continuous application straps 164 and 166, alternatively referred to as strap continuum 164 and strap continuum 166.

Figure 7A:
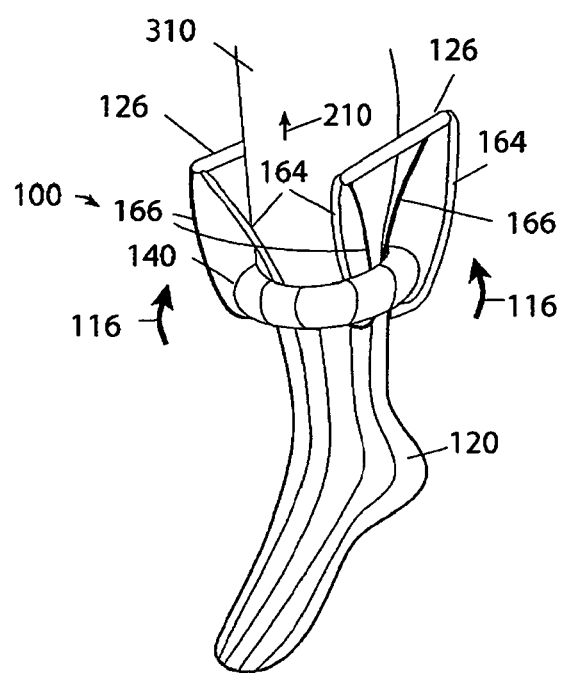
FIGS. 7A-B and 8A-B show a torus including continuous application straps, according to embodiments of the invention.

As seen in FIG. 7A, pulling handles 126 in direction 210 causes elastic tube 120 to unwind from elastic tube roll 140 as torus assembly 100 is moved in proximal direction 210 along extremity 310.

Figure 7B:
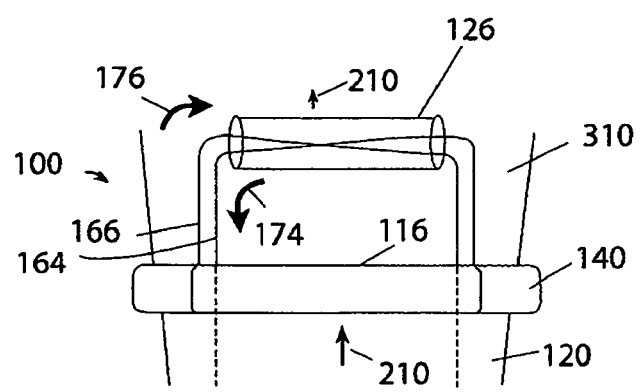

As seen in schematic, in FIG. 7B, strap continuum 166 is wound around an outer surface of elastic tube roll 140 on the left, slidingly passes through handle 126 in a direction 176 and continues on an inner surface of elastic tube 120 on the right.

In contradistinction, strap continuum 164 is wound around an outer surface of elastic tube roll 140 on the right, slidingly passes through handle 126 in a direction 174 and continues on an inner surface of elastic tube 120 on the left.

As handle 126 is pulled in direction 210 the right side of strap continuum 166 elongates with the elongated portion being taken up while being deposited along extremity 310 on the left.

Figure 8A:
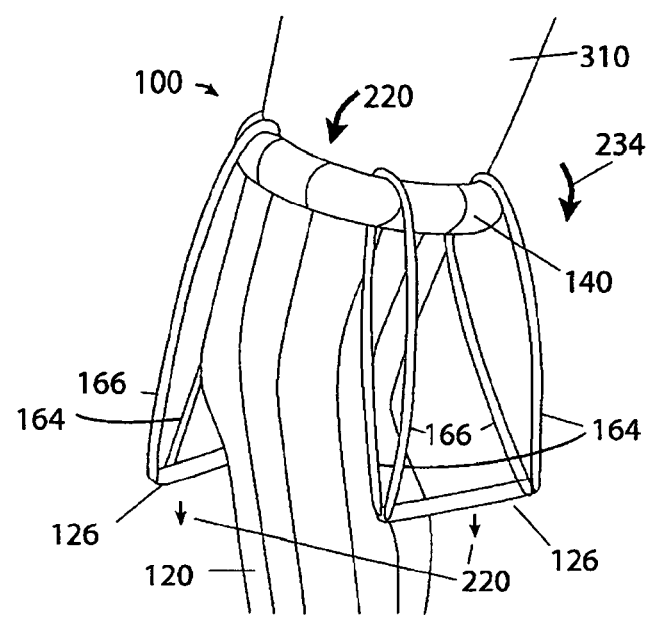
Figure 8B:
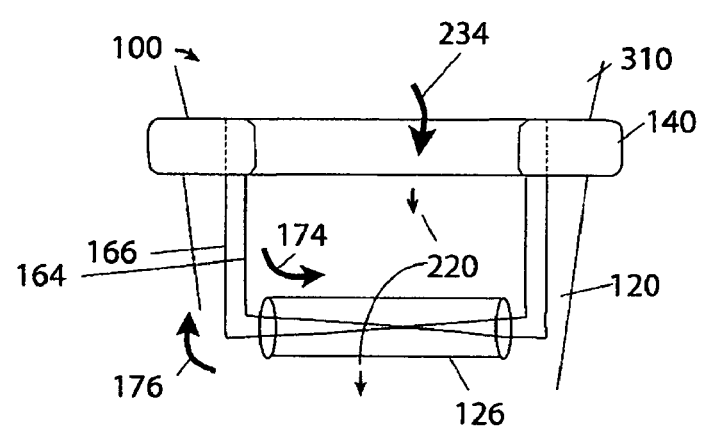

In FIGS. 8A and 8B, handle 126 is shown being pulled in a distal direction 220, and the left side of strap continuum 166 elongates with the elongated portion being taken up while being deposited on the right along extremity 310.

There are still further embodiments which optionally prevent the deployment handles from continuously elongating during application or removal of a torus and tube assembly.

Rigid Hooked Handles

Figure 9A:
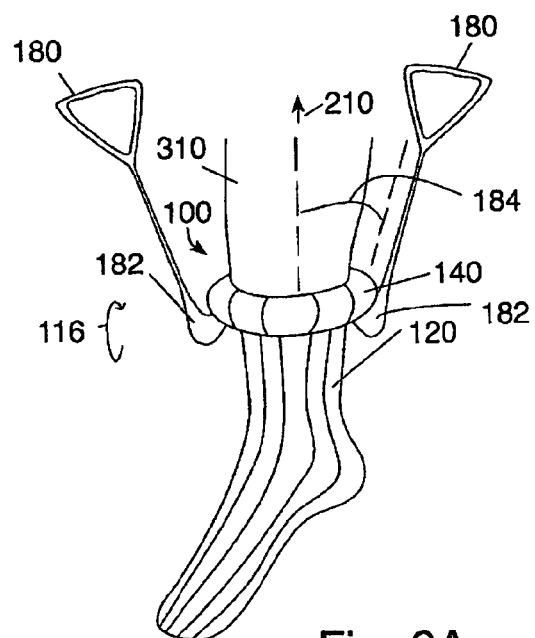
Figure 9B:
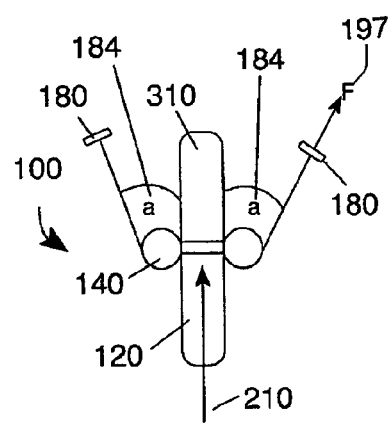
Figure 10:
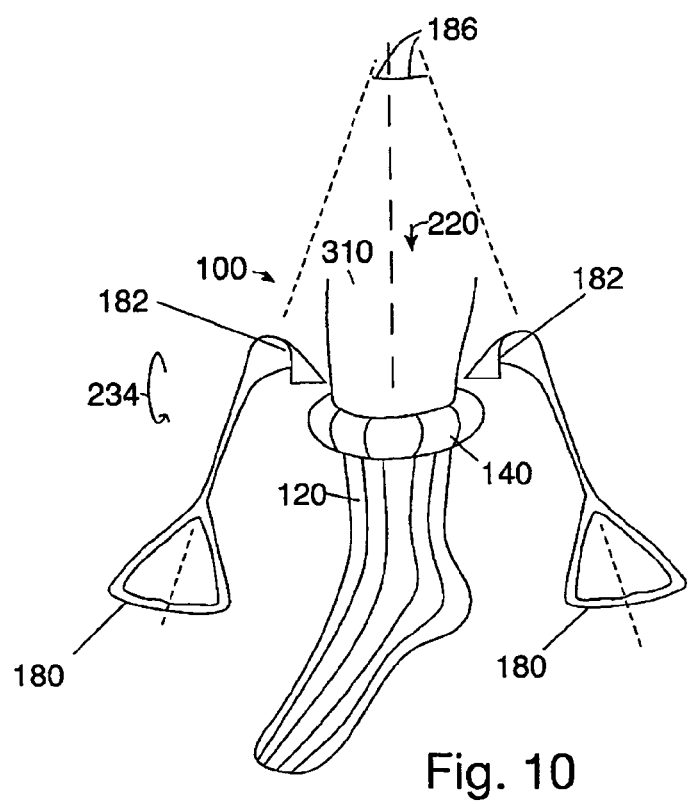

Just one alternative embodiment with non elongating handles is shown in FIGS. 9A-10 in which handles 180 include a hook 182 that pulls elastic tube roll 140 in direction 210 to exsanguinate extremity 310. To remove torus assembly 100, handles 180 are pulled in direction 220 to roll elastic tube roll 140 in a distal direction 220 off extremity 310.

Handles 180 may comprise a rigid material, for example stainless steel, that may be sterilized for multiple uses, while elastic tube 120 may be discarded after each use.

Alternatively, handles 180 may comprise a stretchable material, for example a rubber material, that elongate a specific amount under tension. Such elongation may be 10% of the length of handles 180, 15%, 20% or even 25% of the length of handles 180.

As seen in FIG. 9B, embodiments of torus assembly 100 are optionally optimally applied when the following conditions are met, in which α=angle 184 and force (F)=197:

1. $F^* \cos \alpha \ll F\mu$
2. $F^* R > M\eta$

Where:

Mη—rolling friction moment

R—total device radius (pressure element+sleeve)

Fμ—sliding friction force

Therefore:

$0 < \alpha < \pi/2$—work range, rolling+sliding, favorable range: $0 < \alpha < \pi/3$ $\alpha = \pi/2$—rolling without sliding (around self center)

$\pi/2 < \alpha < \pi$—sliding without rolling

Generally, an optimal angle 184 (α) for rolling torus in a proximal direction 210 is at an angle of between 0 and 60 degrees (between 0 and π/3).

As seen in FIG. 10, an optimal angle 186 (α) for rolling torus 100 in a distal direction 220 is between 120 and 180 degrees (between 0.75 π and π).

It is expected that during the life of this patent many relevant materials and designs for torus exsanguination devices will be developed and the scope of the term "torus exsanguination devices" is intended to include all such new technologies a priori.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A device for exsanguinating a portion of an extremity, the device comprising:
   i) an elastic torus configured to exsanguinate a limb when surrounding an extremity and pulled at a first linear rate in a first direction;
   ii) a handle operatively associated with said elastic torus; and
   iii) at least one elongate attachment element mechanically coupled to said torus to convey pulling force from said handle to said torus,
   wherein a length of said elongate attachment element between said handle and said torus elongates at a different rate than said first rate, during said pulling, further comprising an elongate flexible tube wound around said elastic torus and wherein said at least one elongate attachment element further comprises at least two elongate attachment elements:
   at least one external strap configured to be juxtaposed along an external longitudinal surface of said elongate tube; and
   at least one internal strap configured to be juxtaposed along an internal longitudinal surface of said elongate tube.

2. The device according to claim 1, wherein said elastic torus is configured to twistingly rotate while moving linearly.

3. The device according to claim 1, wherein said at least one elongate attachment element is configured to move said elastic torus in a second linear direction.

4. The device according to claim 1, wherein said elongate flexible tube is configured to progressively unwind from said elastic torus and surround said extremity portion as said elastic torus is moved in said first linear direction.

5. The device according to claim 4, wherein said at least at least two elongate attachment elements are configured to move said elastic torus in a second linear direction.

6. The device according to claim 5, wherein moving said elastic torus in said second linear direction causes said elongate flexible tube to rewind around said elastic torus.

7. The device according to claim 6, wherein said at least one external strap and said at least one internal strap comprise at least one continuum.

8. The device according to claim 7, wherein said at least one continuum is slidingly connected to a handle.

9. A device for exsanguinating a portion of an extremity, the device comprising:
   i) an elastic torus configured to exsanguinate a limb when surrounding an extremity and moving linearly along said extremity, wherein said elastic torus is configured to twistingly rotate while moving linearly;
   ii) an elongate flexible tube wound around said elastic torus, said elongate flexible tube configured to progressively unwind from said elastic torus and surround said extremity portion as said elastic torus is moved in a proximal direction; and
   iii) at least one handle operatively associated with said elastic torus, said at least one handle configured to move said elastic torus along said extremity in both:
   a proximal direction; and
   a distal direction; wherein said handle includes:
   i) at least one external strap configured to be juxtaposed along an external longitudinal surface of said elongate tube; and
   ii) at least one internal strap configured to be juxtaposed along an internal longitudinal surface of said elongate tube; and
   wherein said elongate flexible tube is configured to progressively rewind on said elastic torus as said elastic torus is moved in a distal direction.

10. The device according to claim 9, wherein said at least one handle is configured to optimally roll said torus in a proximal direction when an angle between said extremity and said at least one handle is between 0 and 60 degrees.

11. The device according to claim 9, wherein said at least one handle is configured to optimally roll said torus in a distal direction when an angle between said extremity and said at least one handle is between 120 and 180.

12. The device according to claim 9, wherein said one internal strap forms a continuum with said one external strap and said at least one handle is slidingly juxtaposed along said continuum.

* * * * *